(12) United States Patent
Jiang et al.

(10) Patent No.: US 11,805,992 B2
(45) Date of Patent: Nov. 7, 2023

(54) AUXILIARY VISIBLE LIGHT ROD FOR MULTISOURCE END-EXPIRATORY $CO_2$ MONITORING

(71) Applicant: Shanghai Ninth People's Hospital, Shanghai Jiao Tong University School of Medicine, Shanghai (CN)

(72) Inventors: Hong Jiang, Shanghai (CN); Ming Xia, Shanghai (CN); Yu Sun, Shanghai (CN); Jia Yan, Shanghai (CN)

(73) Assignee: Shanghai Ninth People's Hospital, Shanghai Jiao Tong University School of Medicine, Shanghai (CN)

( * ) Notice: Subject to any disclaimer, the term of this patent is extended or adjusted under 35 U.S.C. 154(b) by 588 days.

(21) Appl. No.: 17/117,147

(22) Filed: Dec. 10, 2020

(65) Prior Publication Data

US 2021/0177302 A1   Jun. 17, 2021

(30) Foreign Application Priority Data

Dec. 11, 2019   (CN) .......................... 201911266418.6

(51) Int. Cl.
*A61B 1/267*   (2006.01)
*A61M 11/00*   (2006.01)
(Continued)

(52) U.S. Cl.
CPC .......... *A61B 1/267* (2013.01); *A61B 1/00147* (2013.01); *A61B 1/07* (2013.01);
(Continued)

(58) Field of Classification Search
CPC ....... A61B 1/267; A61B 1/00147; A61B 1/07; A61B 5/0836; A61B 5/0803; A61B 1/00096; A61B 1/00131; A61B 1/05; A61B 1/0661; A61B 5/0077; A61B 5/6852; A61B 1/2676; A61B 1/00064; A61B 1/04; A61M 11/003; A61M 16/04; A61M 11/006;
(Continued)

(56) References Cited

U.S. PATENT DOCUMENTS

2002/0108610 A1 *  8/2002  Christopher ...... A61M 16/0427
                                                              128/207.15
2007/0049794 A1 *  3/2007  Glassenberg .......... A61B 1/042
                                                              600/179

(Continued)

*Primary Examiner* — Andrey Shostak
(74) *Attorney, Agent, or Firm* — JCIP GLOBAL INC.

(57) ABSTRACT

The present invention discloses an auxiliary visible light rod for multisource end-expiratory $CO_2$ monitoring. The auxiliary visible light rod comprises a handle, a pump body, a medicine compartment, a rod body and a bracket. The handle is separately connected with the medicine compartment, the pump body and the rod body, and one end of the rod body is connected with a rod head. A lamp and an atomizing head are arranged in the rod head. A circuit tube is connected with the external wall of the rod body, one end of the circuit tube is connected with a display screen, and the other end of the circuit tube is connected with a camera in the rod head. The bracket sleeves the rod body and is fixed to the outer side of an oral cavity or a chin of a patient, and thus the stability of the rod body is improved.

5 Claims, 6 Drawing Sheets

(51) Int. Cl.
*A61B 1/07* (2006.01)
*A61B 5/083* (2006.01)
*A61B 1/00* (2006.01)
*A61M 16/04* (2006.01)

(52) U.S. Cl.
CPC ......... *A61B 5/0836* (2013.01); *A61M 11/003* (2014.02); *A61M 16/04* (2013.01)

(58) Field of Classification Search
CPC .. A61M 2016/0413; A61M 2202/0468; A61M 16/0488; A61M 11/00; A61M 31/00; A61M 2210/1032
See application file for complete search history.

(56) References Cited

U.S. PATENT DOCUMENTS

2011/0263935 A1* 10/2011 Qiu ..................... G06F 18/2415
382/128
2017/0258312 A1* 9/2017 Zhou .................. A61B 1/00009

* cited by examiner

AUXILIARY VISIBLE LIGHT ROD FOR MULTISOURCE END-EXPIRATORY $CO_2$ MONITORING

CROSS-REFERENCE TO RELATED APPLICATION

This application claims the priority benefit of China application serial no. 201911266418.6, filed on Dec. 11, 2019. The entirety of the above-mentioned patent application is hereby incorporated by reference herein and made a part of this specification.

TECHNICAL FIELD

The present invention relates to the technical field of medical equipment, in particular to an auxiliary visible light rod for multisource end-expiratory $CO_2$ monitoring.

BACKGROUND

Tracheal intubation is the most effective and reliable method for establishing an artificial airway, and it is also a necessary technique for general anesthesia and emergency resuscitation.

Traditional intubation method is to use direct laryngoscope intubation under direct vision, but the airway conditions of patients are very different. For patients with poor intubation conditions (such as small jaw, short thyromental distance, raised glottis, small opening, limited neck movement), direct laryngoscope intubation is often difficult. The failure rate of the first intubation is high, which requires repeated attempts, takes a long time, and causes patients secondary injuries.

Corresponding improvement solutions have been proposed in response to the above problems. For example, the position of the tracheal intubation in the body can be determined through the monitoring of multisource end-expiratory $CO_2$, which can be easily adjusted and can also improve efficiency. However, this method is not perfect due to its technology, and although it can cooperate with the sensing device to monitor multisource end-expiratory $CO_2$, it has a great dependence on the accuracy of the device. Besides, the deviation of the sensor position, the sensor's failure or disturbances in the data analysis system will have a negative impact on the operation, and there is a lack of intuitive and visible auxiliary methods. The existing light rods are portable, economical, and can solve most of the difficult intubation problems, but they also have disadvantages. For example: first, because of its lack of visibility, it can only rely on the light source to determine the location, and lack of direct observation of the internal environment; secondly, during the insertion and removal of the light rod, the friction with the airway is extremely prone to redness and inflammation when the patient's resistance is poor or the light rod's bacteria exceed the standard.

SUMMARY OF THE INVENTION

The purpose of the present invention is to provide an auxiliary visible light rod for multisource end-expiratory $CO_2$ monitoring, which is capable of observing the inside of a patient's trachea during tracheal intubation and reducing the infection and discomfort caused by intubation given the shortcomings of the prior art.

To solve the above problems, the present invention provides an auxiliary visible light rod for multisource end-expiratory $CO_2$ monitoring, which comprises: a handle, a pump body, a medicine compartment, and a rod body; one end of the handle is connected to the pump body, and the other end connected to the medicine compartment, a first button is provided on the handle; the pump body is connected to the rod body and an atomizing tube provided in the rod body; a second button is provided on the pump body; the medicine compartment comprises an inner cavity. The sidewall of one end of the inner cavity is provided with a thimble, thimble holes and a filter hole, and the sidewall of the other end of the inner cavity is provided with a through-hole. The through-hole is connected to one end of a transfer tube provided inside the handle, and the other end of the transfer tube is connected to the pump body; one end of the rod body is provided with a rod head, and a lamp and an atomizing head are provided in the rod head, and the lamp and the first button are electrically connected through an internal wire, and the atomizing head is connected to the atomizing tube. The circuit tube is connected to the outer wall of the rod body, one end of the wire provided in the circuit tube is connected to the display screen, and the other end of the wire extends into the rod head to be connected to the camera. The bracket includes a collar, a circular frame, a reset member, a first arc frame and a second arc frame; the bracket is sleeved on the rod body through a hole provided on the collar, and one end of the circular frame is connected to the collar, the other end of the circular frame is connected to the reset member, and the first arc frame and the second arc frame are respectively connected to the reset member.

Optionally, an illumination lamp is provided on the pump body; the illumination lamp is provided with an illumination lamp head and a third button.

Optionally, the medicine compartment is provided with a flip cover.

Optionally, the flip cover is provided with a buckle, and the sidewall of the medicine compartment is provided with a clamping groove matching with the buckle.

Optionally, the thimble is installed at the center point of the inner cavity.

Optionally, there are multiple and evenly opened thimble holes at the top of the thimble.

Optionally, the installation height of the lamp and the atomizing head are the same; the installation height of the camera is lower than the installation height of the lamp and the atomizing head.

Optionally, the pump body is connected to the atomizing tube through a flange.

Optionally, an end of the atomizing head is provided with a porous metal mesh.

The present invention provides an auxiliary visible light rod for multisource end-expiratory $CO_2$ monitoring. When tracheal intubation is performed on a patient, the rod head is sent into the patient's trachea through the rod body, and the camera in the rod head and the display screen on the rod body connected to the rod are used to observe the internal environment of the trachea to avoid the difficulties caused by direct laryngoscope intubation. A thimble with a thimble hole is installed in the inner cavity of the medicine compartment so that after piercing the top of the bottled anti-inflammatory agent, it assists the anti-inflammatory agent to enter the pump body through the transfer tube; during the process of removing the light rod, the second button is pressed to trigger the pump body and the anti-inflammatory agent is sprayed into the patient's trachea through the atomizing tube via the atomizing head, so as to achieve the purpose of relieving and anti-inflammatory, and also reduce the probability of bacterial infection and the patient's discomfort. It can also be used to illuminate the oropharynx by a lamp. The present invention can effectively cooperate with tracheal intubation for $CO_2$ monitoring and positioning, and can effectively cooperate with the use of tracheal intubation so that the accuracy rate of tracheal intubation is high, the time consumption is short, and it is not easy to cause secondary damage to patients. During tracheal intubation for a patient, the stability of the rod body during the intubation can be improved by fixing the rod to the external sides of the patient's mouth or the jaw bracket, and the angle of the rod inserted into the patient's trachea can be adjusted during the intubation.

BRIEF DESCRIPTION OF THE DRAWINGS

In order to explain the technical solutions in the embodiments of the present invention or the prior art more clearly, the drawings used in the embodiments or the description of the prior art will be briefly introduced below. Obviously, the drawings in the following description are only some embodiments of the present invention. For those of ordinary skill in the art, other drawings can be obtained based on these drawings without creative efforts.

DETAILED EMBODIMENTS

The specific embodiments of the present invention will be further described in detail below with examples and the accompanying drawings as reference. The following examples of the present invention herein are used to illustrate the present invention, but not intended to limit the scope of the present invention.

Figure 1:
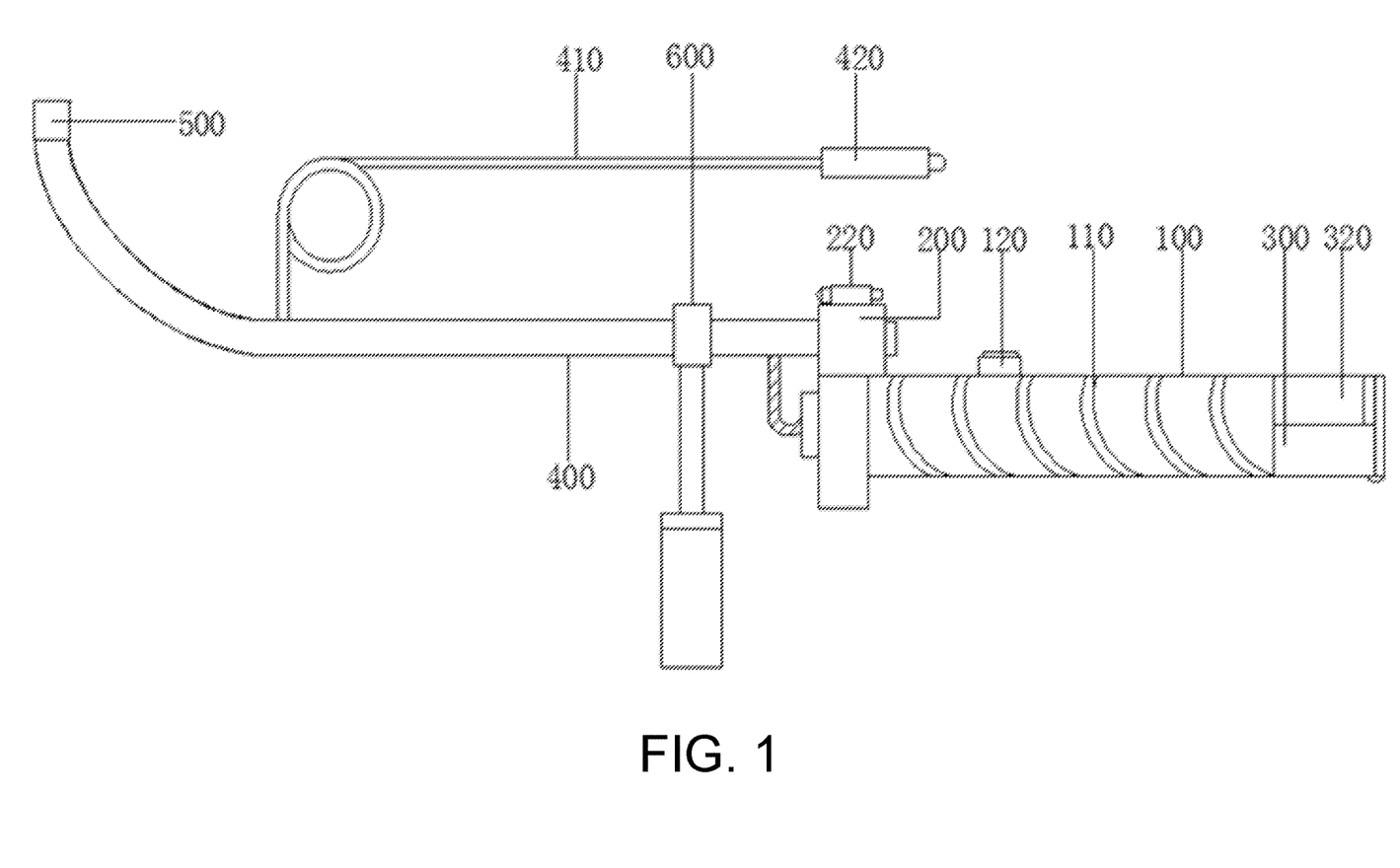
FIG. 1 is a schematic diagram of the overall structure of an auxiliary visible light rod for multisource end-expiratory $CO_2$ monitoring according to an embodiment of the present invention.
Figure 2:
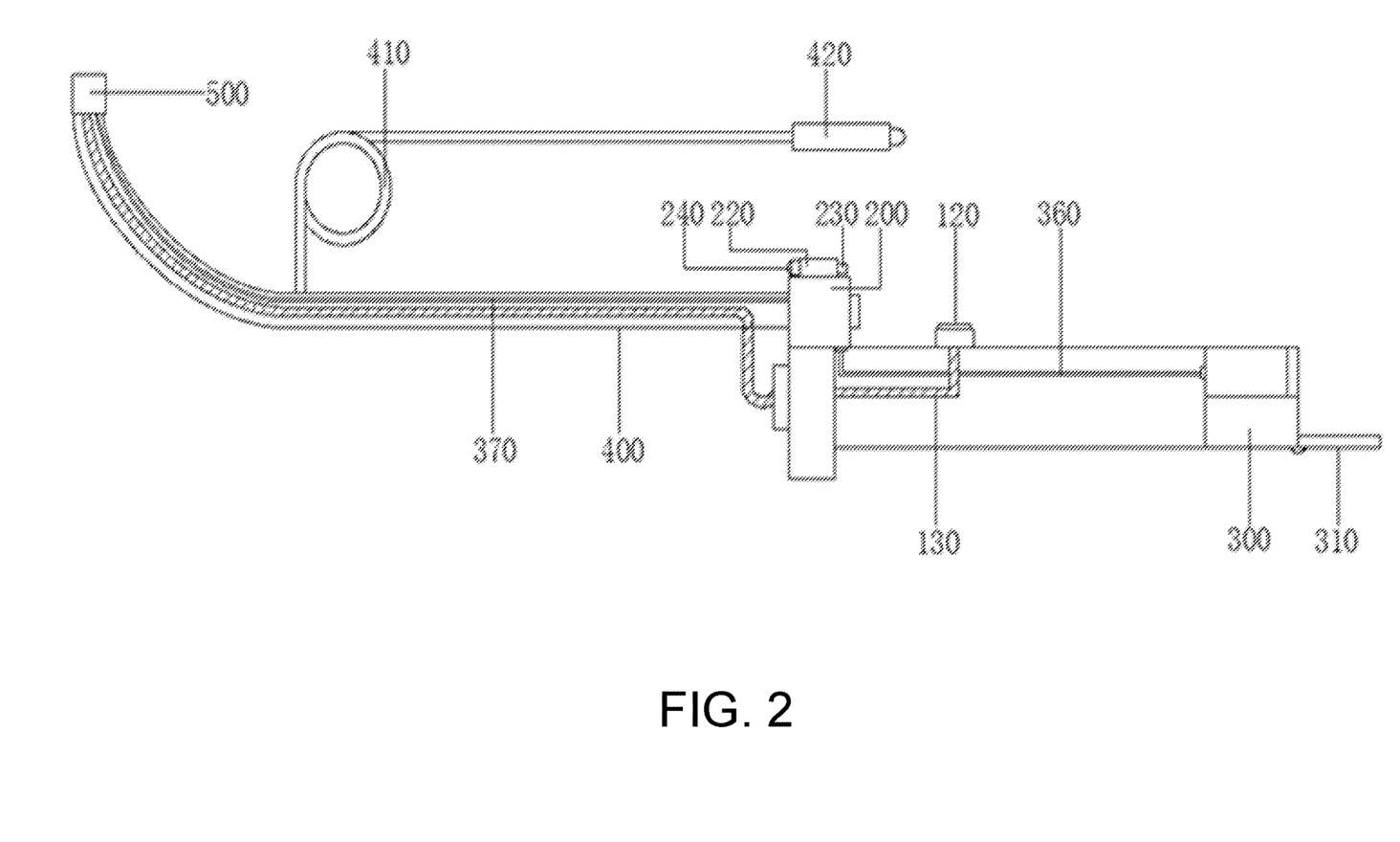
FIG. 2 is a schematic diagram of the internal structure of an auxiliary visible light rod for multisource end-expiratory $CO_2$ monitoring according to an embodiment of the present invention.

As shown in FIG. 1 and FIG. 2, an auxiliary visible light rod for multisource end-expiratory $CO_2$ monitoring provided by an embodiment of the present invention includes a handle 100, a pump body 200, a medicine compartment 300, and a rod body 400. One end of the handle 100 is connected to the pump body 200 and the other end is connected to the medicine compartment 300. A first button 120 is provided on the handle 100. The pump body 200 is connected to the rod body 400 and the atomizing tube 370 provided in the rod body 400. A second button 210 is provided on the pump body 200. In this embodiment, the pump body 200 is placed on the top of the left end of the handle 100, and the bottom of the pump body 200 and the top of the left end of the handle 100 are fixedly connected by screws. The medicine compartment 300 is located on the right side of the handle 100, and the right side wall of the handle 100 and the left side wall of the medicine compartment 300 are fixedly connected by screws. The first button 120 is located on the same side of the pump body 200 on the outer wall of the handle 100 and is fixedly connected to the handle 100 by screws. A second button 210 is provided on the right side wall of the pump body 200. The rod body 400 is located on the left side of the pump body 200. The right end of the rod body 400 is fixedly connected to the left side wall of the pump body 200 by screws. The right end of the atomizing tube 370 provided in the rod body 400 is fixedly connected to the output of the pump body 200 through a flange.

Figure 3:
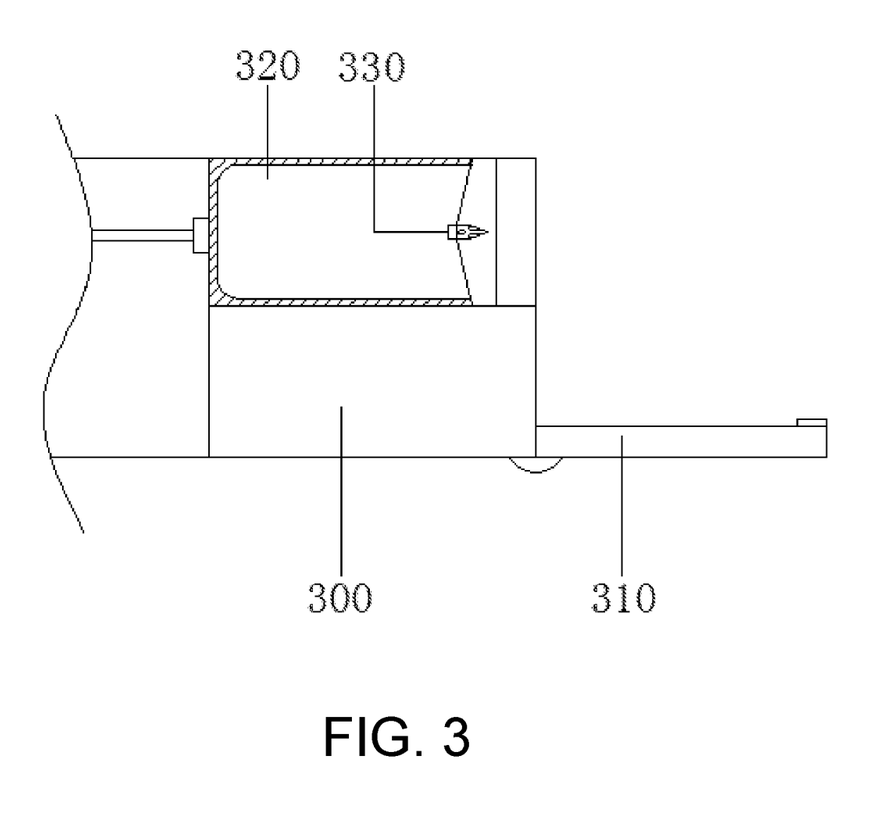
FIG. 3 is a schematic diagram of a medicine compartment of an auxiliary visible light rod for multisource end-expiratory $CO_2$ monitoring according to an embodiment of the present invention.
Figure 4:
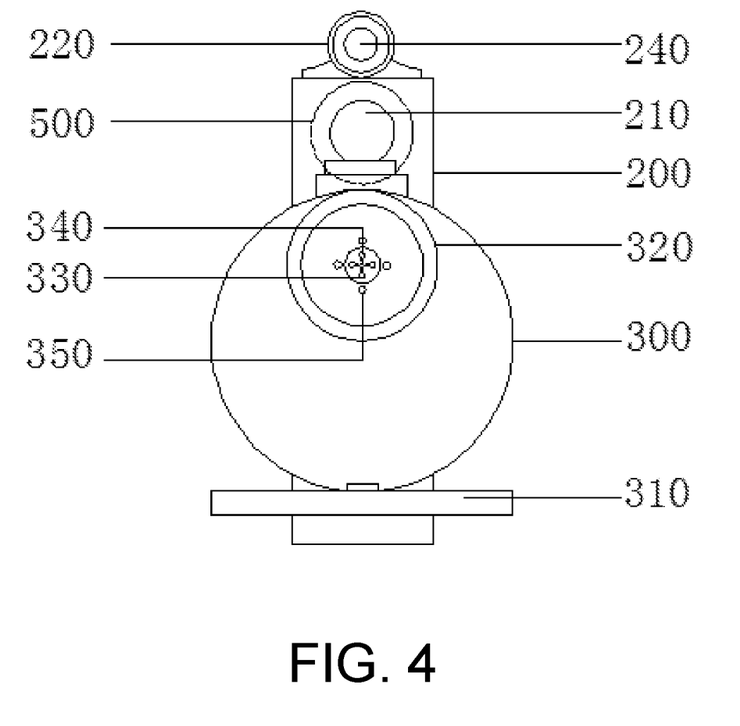
FIG. 4 is a schematic side view of a medicine compartment of an auxiliary visible light rod for multisource end-expiratory $CO_2$ monitoring according to an embodiment of the present invention.

As shown in FIG. 1, FIG. 3 and FIG. 4, the medicine compartment 300 includes an inner cavity 320. A thimble 330, a thimble hole 340, and a filter hole 350 are provided on the sidewall of one end of the inner cavity 320; a through-hole is provided on the sidewall of the other end, and the through-hole is connected to one end of a transfer tube 360 provided in the handle 100. The other end of the transfer tube 360 is connected to the pump body 200. In this embodiment, a thimble 330 is inserted into the right side wall of the inner cavity 320, and a thimble hole 340 and a filter hole 350 are opened on the right side wall of the inner cavity 320; a through-hole is provided on the left side wall of the inner cavity 320. The transfer tube 360 is disposed in the handle 100, and one end thereof is inserted into a through-hole on the left side wall of the inner cavity 320, and the other end thereof is fixedly connected to the input end at the bottom of the pump body 200.

Figure 5:
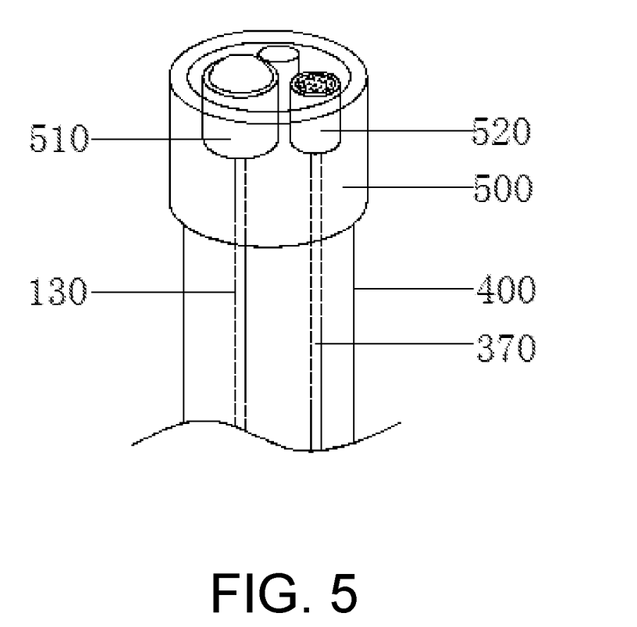
FIG. 5 is a schematic diagram of a rod head of an auxiliary visible light rod for multisource end-expiratory $CO_2$ monitoring according to an embodiment of the present invention.

As shown in FIG. 1, FIG. 2 and FIG. 5, a rod head 500 is provided at one end of the rod body 400. A lamp 510 and an atomizing head 520 are provided in the rod head 500. The lamp 510 is electrically connected to the first button 120 through an internal line 130, and the atomizing head 520 is connected to an atomizing tube 370. In this embodiment, the left end of the rod body 400 and the rod head 500 are fixedly connected with screws. The lamp 510 and the atomizing head 520 are embedded inside the rod head 500. The lamp 510 and the first button 120 are electrically connected through an inner wire 130 partially provided in the rod body 400. The input end of the atomizing head 520 and the left end of the atomizing tube 370 are fixedly connected.

As shown in FIG. 1, FIG. 2 and FIG. 5, circuit tube 410 is connected to the outer wall of the rod body 400. One end of the wire provided in the circuit tube 410 is connected to the display screen 420, and the other end extends into the rod head 500 and is connected to the camera. In this embodiment, circuit tube 410 is plugged into the outer wall of the rod body 400. One end of the wire in the circuit tube 410 is electrically connected to the external display screen 420, and the other end enters the inside of the rod body 400 and extends to the top of the inner cavity of the rod head 500, and a camera is electrically connected to the top.

Figure 6:
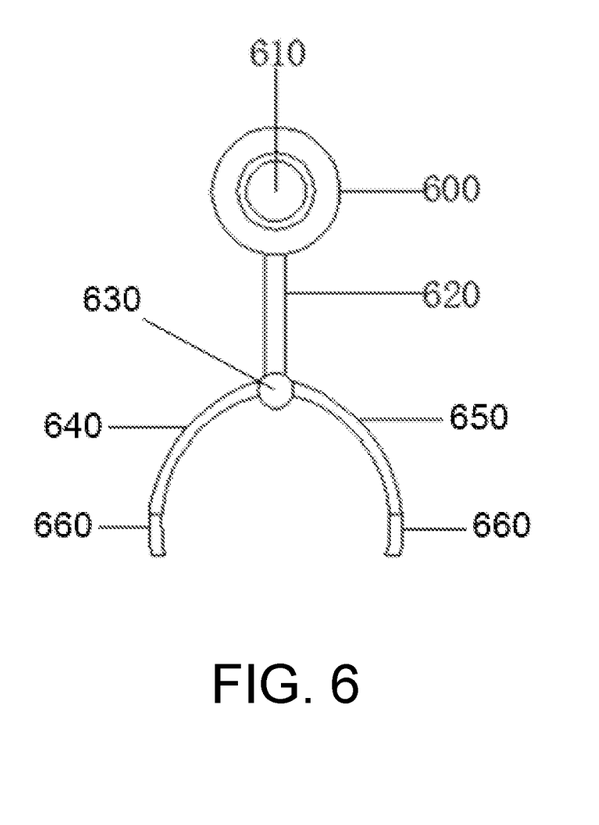
FIG. 6 is a schematic view of a bracket of an auxiliary visible light rod for multisource end-expiratory $CO_2$ monitoring according to an embodiment of the present invention.

As shown in FIGS. 1 and 6, the bracket 600 includes a collar 610, a circular frame 620, a reset member 630, a first arc frame 640, and a second arc frame 650; the bracket 600 is sleeved on the rod body 400 through a hole opened on the collar 610. One end of the circular frame 620 is connected to the collar 610, the other end of the circular frame 620 is connected to the reset member 630, and the first arc frame 640 and the second arc frame 650 are respectively connected to the reset member 630. In this embodiment, the collar 610 is integrally formed with the circular frame 620, and the collar 610 is provided with a hole; a lower end of the circular frame 620 is fixedly connected with a bearing through a screw, and the return spring sleeved with the inner wall of the bearing constitutes a reset member 630; the upper ends of the first arc frame 640 and the second arc frame 650 are movably connected to the outer ring of the bearing, so that the first arc frame 640 and the second arc frame 650 rotate relatively to the connection with the bearing. Both ends of the return spring are fixedly connected to the first arc frame 640 and the second arc frame 650 respectively. A rubber plate is bonded to the inner side wall of the first arc frame 640 and the second arc frame 650, and a rubber block 660 is bonded to the bottom thereof, and the rubber block 660 is a hard rubber plate with a non-slip pattern.

The structure of the reset member 630 is not specifically limited in the embodiment of the present invention, as long as the first arc frame 640 and the second arc frame 650 can be controlled by the reset member 630, so that the first arc frame 640 and the second arc frame 650 can be locked and connected to the patient's face, and thereby the support and positioning function of the rod body 400 through the bracket 600 can be realized.

In this embodiment, the handle 100 is the part that the operator holds when using the device of the present invention; the inner cavity 320 in the medicine compartment 300 is used to store the anti-inflammatory medicine liquid; the anti-inflammatory medicine liquid in the inner cavity 320 is transmitted to the pump body 200 *through* the transfer tube 360; the pump body 200 is used to transmit the anti-inflammatory medicine liquid to the atomization tube head 520 via the atomization tube 370; the rod body 400 is used to receive the atomization tube 370, the inner line 130 and a part of the circuit tube 410, and to support and position the rod head 500; the rod head 500 is used to receive the lamp 510, the atomizing head 520 and the camera. The first button 120 is used to control the switch of the lamp 510; the second button 210 is used to control the operation and stop of the pump body 200. The stent 600 is sleeved on the rod body 400 and is used to increase the stability of the rod body 400 during tracheal intubation.

In one embodiment, as shown in FIG. 1, FIG. 2 and FIG. 4, the pump body 200 is provided with an illumination lamp 220; the illumination lamp 220 is provided with an illumination lamp head 240 and a third button 230. The illumination lamp 220 is placed on the top of the pump body 200 and is fixedly connected to the pump body 200 by screws. An illumination lamp head 240 is screwed to the left side of the illumination lamp 220. A third button 230 is embedded on the right side of the illumination lamp 220 for controlling the illumination lamp head 240 to be turned on and off.

In one embodiment, as shown in FIG. 2, FIG. 3 and FIG. 4, the medicine compartment 300 is provided with a flip cover 310, the flip cover 310 is provided with a buckle, and the side wall of the medicine compartment 300 is provided with a groove matching with the buckle. The flip cover 310 is disposed at the open end on the right side of the medicine compartment 300, and the flip cover 310 is movably connected to the medicine compartment 300 through a hinge. There is a buckle integrally formed on the left side of the flip cover 310, and a clamping groove matching the buckle of the flip cover 310 is provided on the opening side wall of the medicine compartment 300. Through the cooperation of the buckle and the clamping groove, the flap 310 can be closed and opened to the open end of the medicine compartment 300.

In one embodiment, as shown in FIG. 3 and FIG. 4, the thimble 330 is installed at the center point of the inner cavity 320, and a plurality of thimble holes 340 are evenly opened at the top of the thimble 330, so as to facilitate the penetration of the rubber seal cover of the anti-inflammatory medicinal solution bottle and guide the medicinal solution into the medicine compartment 300. In this embodiment, the thimble 330 has a triangular shape, and the inner cavity 320 has a funnel shape, which are not specifically limited in this embodiment of the present invention.

In one embodiment, as shown in FIG. 5, in the rod head 500, the installation height of the lamp 510 and the atomizing head 520 are the same, and the installation height of the camera is slightly lower than the installation height of the lamp 510 and the atomizing head 520. Therefore, the camera does not block the lamp 510 and the atomizing head 520. In order to obtain a clear image of a patient's trachea, the camera may be a high-definition camera, which is not specifically limited in the embodiment of the present invention. In order to improve the visual effect, the lamp 510 may be a high-brightness red light emitter, which is not specifically limited in the embodiment of the present invention.

In one embodiment, in order to effectively limit the lamp 510, the atomizing head 520 and the camera, a circumferential inner wall of the rod head 500 is inlaid with a porous pad, and the top of the porous pad is provided with round holes matching the lamp 510, the atomizing head 520 and the camera.

In one embodiment, in order to protect the position of the atomizing head 520, a porous metal mesh is adhered to the output end of the atomizing head 520.

In one embodiment, as shown in FIG. 1, the handle 100 is a cylinder, and the outer wall is provided with twill 110 to facilitate holding in use.

In one embodiment, in order to ensure the safety of the patient, the rod body 400, the circuit tube 410, and the rod head 500 may be made of medical-grade materials, which is not specifically limited in the embodiment of the present invention.

When the present invention is specifically used, firstly, the positions of the thyroid cartilage and the trachea of the patient are determined by observation. Then, open the flip cover 310 of the medicine compartment 300, and use the thimble 330 on the side wall of the inner cavity 320 to pierce the rubber sealing plug of the anti-inflammatory medicine liquid, so that the medicine liquid enters the inner cavity 320 through the thimble hole 340 and/or the filter hole 350, and passes through the transfer tube 360 connected to the inner cavity 320 to allow the medicinal solution to enter the pump body 200. The anti-inflammatory medicinal solution may also be directly poured into the inner cavity 320 of the medicine compartment 300.

Secondly, place a small cushion on the patient's neck to make the patient's head tilt back slightly to facilitate the patient's mouth opening. Then, pull the first arc frame 640 and the second arc frame 650 to make the first arc frame 640 and the second arc frame 650 unfolded and clamped on both sides of the patient's oral cavity or at the chin position, and the bracket 600 is clamped to the outside of the patient's oral cavity by means of the restoring force of a return spring connected to the first and second arc frames 640 and 650. The rubber plate adhered to the inner wall of the first arc frame 640 and the second arc frame 650 and the rubber block 660 adhered to the bottom thereof will increase the friction force, so that the bracket 600 is more stably fixed to the patient's face, and the skin of patient can be protected. Next, gently lift the patient's lower jaw forward and upward to increase the distance between the patient's upper and lower incisors and create a free space for the insertion of the visible light rod. At this time, pressing the first button 120 turns on the lamp 510 in the rod head 500, and pressing the third button 230 turns on the illumination lamp head 240 of the illumination lamp 220, which is used to illuminate the patient's oropharynx during the intubation process to facilitate observation of the condition of the pharynx of the patient. During the use, it can be determined whether the lamp 510 and the illumination lamp head 240 need to be turned on at the same time according to the needs of the implementation.

Next, hold the handle 100 in a pen-style manner, and gently insert the rod body 400 of the visible light rod with the tracheal tube into the deep part of the patient's throat along the natural arc of the throat. At the same time, rotate the rod body 400 of the visible light rod by 15° to 20° clockwise until the bright spot of the lamp 510 in the head 500 appears at a deeper level than the thyroid cartilage, at the position of the gap between the trachea and the muscle; then gently rotate the rod body 400 counterclockwise (at this time, it is usually unable to rotate counterclockwise and will be blocked), and retract the rod body 400 of the visible light rod at the same time. When the resistance to rotation in the counterclockwise direction disappears, usually the light of the lamp 510 can illuminate the trachea instantly. At this time, maintain the current position of the rod 500, and rotate it back and forth slightly clockwise and counterclockwise to find the best position of the light that illuminates the trachea, then gently forward the rod 400 by 2~3 cm across the vocal cords, hold the position of the rod 400 with one's right hand, release the patient's jaw with one's left hand, hold the tracheal tube forward along the visible light rod into the trachea. Carefully observe the characteristics and location of the light spot formed by the lamp 510 on the neck and the distance to the thyroid cartilage and trachea, and adjust it dynamically to find the best position to illuminate the ventilation tube. At this time, the camera at the end of the circuit tube 410 in the rod head 500 can display the condition inside the trachea on the display screen 420 at that time, and can understand the internal condition of the patient's trachea more intuitively.

During the intubation, the bracket 600 sleeved on the rod 400 can provide support and positioning for the rod 400, which not only improves the stability of the rod 400 during the intubation, but also facilitates the rod body during the intubation. The angle at which the 400 is inserted into the trachea of the patient is adjusted accordingly to improve the efficiency of intubation.

When exiting the light rod, hold the handle 100 to apply force in the opposite direction, and simultaneously press the second button 210 on the pump body 200, so that the anti-inflammatory medicine liquid flows through the atomizing tube 370 through the pump body 200 and passes through the atomizing head 520 in rod head 500 to be sprayed into the corresponding part in the trachea of the patient, so that the inside of the trachea can be relieved and anti-inflammatory, and the probability of internal infection and the discomfort of the patient can be effectively reduced. Then, relieve the first arc frame 640 and the second arc frame 650 that are clipped to the sides of the patient's mouth or at the chin, the bracket 600 is removed from the patient's face.

The present invention provides an auxiliary visible light rod for multisource end-expiratory $CO_2$ monitoring. At the time of intubation for a patient, the rod head is sent to the patient's trachea through the rod body. The cameras in the rod head and the rod body are connected to the rod body. The upper display screen observes the inside of the trachea to avoid the difficulties caused by direct laryngoscope intubation. A thimble with thimble holes is installed in the inner cavity of the medicine compartment. After piercing the top of the bottled anti-inflammatory agent, the anti-inflammatory agent enters the pump body through the transfer tube; during the process of removing the light rod, press the second button to trigger the pump body and spray the anti-inflammatory agent into the patient's trachea through the atomizing tube, so as to relieve the anti-inflammatory purpose, and also reduce the probability of bacterial infection and the patient's discomfort. The oropharynx can also be illuminated by a lamp. The present invention can be used with tracheal intubation for $CO_2$ monitoring and positioning, and can effectively be used with tracheal intubation, so that the accuracy of tracheal intubation is high, the time is short, and it is not easy to cause side damage to patients. During tracheal intubation for a patient, the stability of the rod during the intubation can be improved by fixing the rod to the external sides of the patient's mouth or the jaw bracket, and the angle of the rod inserted into the patient's trachea can be adjusted during the intubation.

In the description of the present invention, it should be noted that the terms "installed", "connected with", and "connected to" should be understood in a broad sense unless otherwise specified and limited. For example, it can be a fixed connection, a detachable connection, or an integrated connection; it can be a mechanical connection or an electrical connection; it can be a direct connection or an indirect connection through an intermediate medium, and it also can be the internal connection of two components. For those of ordinary skill in the art, the specific meaning of the above terms in the invention can be understood in specific circumstances, and should not be understood as a limitation of the invention.

The above embodiments are only used to illustrate the present invention, but are not intended to limit the present invention. Although the present invention has been described in detail with reference to the embodiments, those of ordinary skill in the art should understand that various combinations, modifications, or equivalent replacements of the technical solutions of the present invention shall not depart from the spirit and scope of the technical solutions of the present invention, and shall all fall within the scope of the claims of the present invention.

It should be noted that the terminology used herein is for the purpose of describing particular embodiments only and is not intended to be the limiting of the exemplary embodiments according to the present application. As used herein, the singular forms are intended to include the plural forms as well, unless the context clearly indicates otherwise. It will be further understood that the terms "comprises" or "includes" when used in this specification, specify the presence of stated features, steps, operations, elements, components and/or combinations thereof.

In the present invention, terms such as "up", "down", "left", "right", "front", "rear", "vertical", "horizontal", "side", "bottom" that indicate the orientation or positional relationship are based on the orientation or positional relationship shown in the Figures, and is only a relational term determined for the convenience of describing the structural relationship of each component or element of the present invention, and does not specifically refer to any component or element in the present invention, and should not be understood as the limiting of the present invention.

The above descriptions are merely preferred embodiments of the present invention and are not intended to limit the present invention. For those skilled in the art, the present invention may have various modifications and changes. Any modification, equivalent replacement, and improvement made within the spirit and principle of the present invention shall be included in the protection scope of the present invention.

What is claimed is:

1. An auxiliary visible light rod for multisource end-expiratory $CO_2$ monitoring, comprising:
a handle, a pump body, a medicine compartment, a rod body and a bracket, wherein:
one end of the handle is connected to the pump body, and the other end of the handle is connected to the medicine compartment, and a first button is provided on the handle;
the pump body is connected to the rod body and an atomizing tube provided within the rod body; a second button is provided on the pump body;
the medicine compartment comprises an inner cavity, and a side wall of one end of the inner cavity is provided with a thimble, thimble holes and a filter hole, and a side wall of the other end of the inner cavity is provided with a through hole, and the through hole is connected to one end of a transfer tube provided inside the handle, and the other end of the transfer tube is connected to the pump body; the thimble holes are multiple and evenly arranged at a top of the thimble; the thimble is installed at a center point of the inner cavity; the medicine compartment is provided with a flip cover, the flip cover is provided with a buckle, and the medicine compartment is provided with a clamping groove matching with the buckle;
a rod head is provided at one end of the rod body, and a lamp and an atomizing head are provided in the rod head, the lamp and the first button are electrically connected through an inner wire, and the atomizing head is connected to the atomizing tube;
a circuit tube is connected to an outer wall of the rod body, one end of a wire provided inside the circuit tube is connected to a display screen, and the other end of the wire extends into the rod head to connect with a camera;
the bracket comprises a collar, a circular frame, a reset member, a first arc frame and a second arc frame; the bracket is sleeved on the rod body through holes on the collar, one end of the circular frame is connected to the collar, and the other end of the circular frame is connected to the reset member, and the first arc frame and the second arc frame are respectively connected to the rest member.

2. The auxiliary visible light rod for multisource end-expiratory $CO_2$ monitoring according to claim 1, wherein the pump body is provided with an illumination lamp; the illumination lamp is provided with an illumination lamp head and a third button.

3. The auxiliary visible light rod for multisource end-expiratory $CO_2$ monitoring according to claim 1, wherein installation heights of the lamp and the atomizing head are the same, and an installation height of the camera is lower than the installation heights of the lamp and the atomizing head.

4. The auxiliary visible light rod for multisource end-expiratory $CO_2$ monitoring according to claim 1, wherein the pump body is connected to the atomizing tube through a flange.

5. The auxiliary visible light rod for multisource end-expiratory $CO_2$ monitoring according to claim 1, wherein a porous metal wire mesh is provided at an end of the atomizing head.

* * * * *